United States Patent
Nishi

(10) Patent No.: US 6,596,292 B2
(45) Date of Patent: Jul. 22, 2003

(54) SOLID PESTICIDAL FORMULATION

(75) Inventor: Shugo Nishi, Minoo (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/818,514

(22) Filed: Mar. 28, 2001

(65) Prior Publication Data

US 2002/0019441 A1 Feb. 14, 2002

(30) Foreign Application Priority Data

Jun. 22, 2000 (JP) ........................................ 2000-187472

(51) Int. Cl.$^7$ ................................................. A01N 25/12
(52) U.S. Cl. ........................ 424/409; 424/405; 424/408; 424/417; 424/421
(58) Field of Search ................................. 424/409, 417, 424/421, 408; 504/101, 116.1, 150, 174, 184

(56) References Cited

U.S. PATENT DOCUMENTS

| 3,143,407 A | 8/1964 | Mitchell et al. |
| 4,867,972 A | 9/1989 | Girardeau et al. |
| 5,232,701 A | 8/1993 | Ogawa et al. |

FOREIGN PATENT DOCUMENTS

| EP | 0 480 679 A1 | | 4/1992 |
| JP | 56 57702 | * | 5/1981 |
| JP | 62-263101 | | 11/1987 |
| WO | 93/13658 | | 7/1993 |
| WO | 9715186 | * | 5/1997 |

OTHER PUBLICATIONS

Database WPI, Section Ch, Week 198127, Derwent Publication Ltd.
Patent Abstracts of Japan, vol. 031, No. 236 (C–602), May 30, 1989.

* cited by examiner

Primary Examiner—Neil S. Levy
(74) Attorney, Agent, or Firm—Sughrue Mion, PLLC

(57) ABSTRACT

A solid pesticidal formulation which comprises (a) 0.1 to 75% by weight of a pesticidal active ingredient, (b) 0.3 to 40% by weight of a dispersant, (c) 0.3 to 20% by weight of a wetting agent, (d) 0.1 to 30% by weight of a boron compound selected from the group of boron oxide, boric acid and borate, (e) 0.1 to 95% by weight of a water-soluble carrier and (f) 0.1 to 30% by weight of smectite that is excellent in preservation stability and can prevent aggregation of formulation, reducing of fluidity, and reducing dispersibility when dilution with water is applied.

15 Claims, No Drawings

SOLID PESTICIDAL FORMULATION

FIELD OF THE INVENTION

The present invention relates to a solid pesticidal formulation.

BACKGROUND ART

Pesticides are usually used in various type formulations for applying the active ingredient easily and effectively. Formulations applied as an aqueous dilution include liquid formulations such as emulsifiable concentrate, aqueous solution, suspension concentrate and emulsion in water, and solid formulations such as wettable powder, water soluble powder and water dispersible granule. Among them, solid formulations are preferable because they are packed in the paper bag or film which can be folded after use and which is a convenient container.

However, solid formulations may cause a trouble of coagulation of the formulation or reducing of fluidity when they are placed in the air in open package in the case of application or when they are placed in the air while the prepared formulation is divided and packed, because of their hygroscopic character originated from the used materials, for examples, the hygroscopic character of active ingredient, carrier, surfactant and so on. Further, the solid formulations for aqueous spray application, for examples, wettable powder, water dispersible granule and so on, may reduce dispersibility when they are diluted with water, even if coaguration or reducing of fluidity is not observed. The reduced dispersibility when diluted with water may cause uneven application from heterogeneous dilution or clogging of spray nozzle from aggregation in the dilution or precipitation of insoluble materials. As a result, when applying pesticides, desired efficacy may not be observed or undesired phytotoxicity may be caused to give a severe problem. Furthermore, granular formulations may also reduce the hardness of the particles or deteriorate disintegration in water. Especially, the formulations containing water soluble carrier or water soluble active ingredient often cause these troubles.

SUMMARY OF THE INVENTION

The present invention provides a solid formulation having excellent preservative stability, and it comprises a specific amount of pesticidal active ingredient, dispersant, wetting agent, water-soluble carrier, smectite and boron compound selected from the group of boron oxide, boric acid and borate.

Namely, the present invention provides a solid pesticidal composition which comprises (a) 0.1 to 75% by weight of a pesticidal active ingredient, (b) 0.3 to 40% by weight of a dispersant, (c) 0.3 to 20% by weight of a wetting agent, (d) 0.1 to 30% by weight of a boron compound selected from the group of boron oxide, boric acid and borate, (e) 0.1 to 95% by weight of a water-soluble carrier and (f) 0.1 to 30% by weight of smectite.

DETAILED DESCRIPTION OF THE INVENTION

The pesticidal active ingredient used for controlling harmful pests or regulating plant growth in the present invention is not limited and may be water soluble or water insoluble. Its melting point is also not limited. Examples are as follows, and the active ingredient may be one isomer or a mixture of two or more isomers including geometrical isomers, optical isomers and so on.

Organophosphosphorus compounds such as O,O-dimethyl O-(3-methyl-4-nitrophenyl)phosphorothioate, O,O-dimethyl O-[3-methyl-4-(methylthio)phenyl] phosphorothioate, O,O-diethyl O-(2-isopropyl-6-methylpyrimidin-4-yl)phosphorothioate, O,O-diethyl O-3,5,6-trichloro-2-pyridyl phosphorothioate, O,S-dimethyl acetylphosphoramidothioate S-2,3-dihydro-5-methoxy-2-oxo-1,3,4-thiadiazol-3-ylmethyl O,O-dimethyl phosphorodithioate, O,O-diethyl S-2-ethylthioethyl phosphorodithioate, 2,2-dichlorovinyl dimethylphosphate, O-ethyl O-4-(methylthio)phenyl S-propyl phosphorodithioate, O-4-cyanophenyl O,O-dimethyl phosphorothioate, 2-methoxy-4H-1,3,2-benzodioxaphosphorin-2-sulfide, O,O-dimethyl S-(N-methylcarbamoylmethyl)dithiophosphate, ethyl 2-dimethoxyphosphinothioylthio(phenyl)acetate, diethyl (dimethoxyphosphinothioylthio)succinate, dimethyl 2,2,2-trichloro-1-hydroxyethylphosphonate, S-3,4-dihydro-4-oxo-1,2,3-benzotriazin-3-ylmethyl O,O-dimethyl phosphorodithioate, dimethyl [(E)-1-methyl-2-(methylcarbamoyl)vinyl]phosphate, O,O,O',O'-tetraethyl-S,S'-methylenebis(phosphorodithioate), O-2,6-dichloro-4-methylphenyl O,O-dimethyl phosphorothioate and so on;

Carbamate compounds such as 2-sec-butylphenyl methylcarbamate, ethyl N-[2,3-dihydro-2,2-dimethylbenzofuran-7-yloxycarbonyl(methyl)aminothio]-N-isopropyl-β-alaninate, 2-isopropoxyphenyl N-methylcarbamate, 2,3-dihydro-2,2-dimethyl-7-benzo[b] furanyl N-dibutylaminothio-N-methylcarbamate, 1-naphthyl N-methylcarbamate, S-methyl N-(methylcarbamoyloxy)thioacetimidate, 2-(ethylthiomethyl)phenyl methylcarbamate, 2-methyl-2-(methylthio)propionaldehyde O-methylcarbamoyloxime, N,N-dimethyl-2-methylcarbamoyloxyimino-2-(methylthio) acetamide, S-4-phenoxybutyl N,N-dimethylthiocarbamate and so on;

Pyrethroid compounds such as 2-(4-ethoxyphenyl)-2-methyl-1-(3-phenoxybenzyl)oxypropane, (RS)-α-cyano-3-phenoxybenzyl (RS)-2-(4-chlorophenyl)-3-methylbutyrate, (S)-α-cyano-3-phenoxybenzyl (S)-2-(4-chlorophenyl)-3-methylbutyrate, (RS)-α-cyano-3-phenoxybenzyl 2,2,3,3-tetramethylcyclopropanecarboxylate, (RS)-α-cyano-3-phenoxybenzyl (1RS)-cis,trans-3-(2,2-dichlorovinyl)-2,2-dimethylcyclopropanecarboxylate, 3-phenoxybenzyl (1RS)-cis,trans-3-(2,2-dichlorovinyl)-2,2-dimethylcyclopropanecarboxylate, (RS)-α-cyano-3-phenoxybenzyl (1RS,3Z)-cis-3-(2-chloro-3,3,3-trifluoroprop-1-enyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (RS)-2,2-dichloro-1-(4-ethoxyphenyl) cyclopropanecarboxylate, α-cyano-3-phenoxybenzyl N-(2-chloro-α,α,α-trifluoro-p-tolyl)-D-valinate, 2-methyl-3-phenylbenzyl (1RS,3Z)-cis-3-(2-chloro-3,3,3-trifluoro-1-propenyl)-2,2-dimethylcyclopropanecarboxylate, 2-(4-bromodifluoromethoxyphenyl)-2-methyl-1-(3-phenoxybenzyl)methylpropane, (S)-α-cyano-3-phenoxybenzyl (1R)-cis-3-(1,2,2,2-tetrabromoethyl)-2,2-dimethylcyclopropanecarboxylate, (4-ethoxyphenyl)-[3-(4-fluoro-3-phenoxyphenyl)propyl]dimethylsilane, 3-phenoxybenzyl (1R)-cis,trans-2,2-dimethyl-3-(2-methyl-1-propenyl)cyclopropanecarboxylate, (RS)-α-cyano-3-phenoxybenzyl (1R)-cis,trans-2,2-dimethyl-3-(2-methyl-1-propenyl)cyclopropanecarboxylate, 5-benzyl-3-furylmethyl (1R)-cis,trans-2,2-dimethyl-3-(2-methyl-1-propenyl) cyclopropanecarboxylate, (S)-α-cyano-3-phenoxybenzyl (1R,3Z)-cis-(2,2-dimethyl-3-[3-oxo-3-(1,1,1,3,3,3-hexafluoropropyloxy)propenyl]cyclopropanecarboxylate, (RS)-α-cyano-4-fluoro-3-phenoxybenzyl 3-(2,2-dichlorovinyl)-2,2-dimethylcyclopropanecarboxylate, 2,3,5,6-tetrafluoro-4-methylbenzyl (1RS,3Z)-cis-3-(2-chloro-3,3,3-trifluoro-1-propenyl)-2,2-dimethylcyclopropanecarboxylate, 2,3,5,6-tetrafluorobenzyl (1R)-trans-3-(2,2-dichlorovinyl)-2,2-dimethylcyclopropanecarboxylate, 3,4,5,6-tetrahydrophthalimidomethyl (1RS)-cis,trans-2,2-dimethyl-3-(2-methyl-1-propenyl)cyclopropanecarboxylate, (RS)-2-methyl-4-oxo-3-(2-propenyl)-2-cyclopenten-1-yl (1RS)-cis,trans-2,2-dimethyl-3-(2-methyl-1-propenyl) cyclopropanecarboxylate, (S)-2-methyl-4-oxo-3-(2-propynyl)-2-cyclopenten-1-yl (1R)-cis,trans-2,2-dimethyl-3-(2-methyl-1-propenyl)cyclopropanecarboxylate, (RS)-1-ethynyl-2-methyl-2-pentenyl (1R)-cis,trans-2,2-dimethyl-3-(2-methyl-1-propenyl)cyclopropanecarboxylate, 2,5-dioxo-3-(2-propynyl)imidazolidin-1-ylmethyl (1R)-cis,trans-2,2-dimethyl-3-(2-methyl-1-propenyl) cyclopropanecarboxylate, 5-(2-propynyl)furfuryl (1R)-cis, trans-2,2-dimethyl-3-(2-methyl-1-propenyl) cyclopropanecarboxylate, 5-(2-propynyl)furfuryl 2,2,3,3-tetramethylcyclopropanecarboxylate and so on;

Amino acid compounds such as N-(phosphonomethyl) glycine, agriculturally acceptable salt thereof, 4-hydroxymethylphosphinoyl-L-homoalanyl-L-alanine and so on;

Thiadiazine derivatives such as 3-isopropyl-1H-2,1,3-benzothiadiazin-4(3H)-on 2,2-dioxide, 2-tert-butylimino-3-isopropyl-5-phenyl-1,3,5-thiadiazin-4-one and so on;

Nitroimidazolidine derivatives;

Nereistoxin derivatives such as S,S'-(2-dimethylaminotrimethylene) bis(thiocarbamate), N,N-dimethyl-1,2,3-trithian-5-ylamine, S,S'-2-dimethylaminotrimethylene di(benzenethiosulfonate) and so on;

N-cyanoamidine derivatives such as N-cyano-N'-methyl-N'-(6-chloro-3-pyridylmethyl)acetamidine and so on;

Chlorinated hydrocarbon compounds such as 6,7,8,9,10,10-hexachloro-1,5,5a,6,9,9a-hexahydro-6,9-methano-2,4,3-benzodioxathiepineoxide, 1,2,3,4,5,6-hexachlorocyclohexane, 1,1-bis(4-chlorophenyl)-2,2,2-trichloroethanol and so on;

Benzoylphenylurea compounds such as 1-[3,5-dichloro-4-(3-chloro-5-trifluoromethylpyridin-2-yloxy)phenyl]-3-(2,6-difluorobenzoyl)urea, 1-(3,5-dichloro-2,4-difluorophenyl)-3-(2,6-difluorobenzoyl)urea, 1-[4-(2-chloro-4-trifluoromethylphenoxy)-2-fluorophenyl]-3-(2,6-difluorobenzoyl)urea and so on;

Formamidine derivatives such as N,N'-[(methylimino) dimethylidine]-di-2,4-xylidine, N'-(4-chloro-2-methylphenyl)-N,N-dimethylmethynimidamide and so on;

Thiourea derivatives such as N-(2,6-diisopropyl-4-phenoxyphenyl)-N'-tert-butylcarbodiimide and so on;

N-phenylpyrazole compounds;

5-methoxy-3-(2-methoxyphenyl)-1,3,4-oxadiazol-2-(3H)-one, isopropyl 4,4'-dibromobenzylate, 4-chlorophenyl 2,4,5-trichlorophenyl sulfone, S,S-6-methylquinoxalin-2,3-diyl dithiocarbonate, 2-(4-tert-butylphenoxy) cyclohexylprop-2-yl sulfite, bis[tris(2-methyl-2-phenylpropyl)tin]oxide, (4RS,5RS)-5-(4-chlorophenyl)-N-cyclohexyl-4-methyl-2-oxo-1,3-thiazolidine-3-carboxamide, 3,6-bis(2-chlorophenyl)-1,2,4,5-tetrazine, 2-tert-butyl-5-(4-tert-butylbenzylthio)-4-chloropyridazin-3 (2H)-one, tert-butyl (E)-4-[(1,3-dimethyl-5-phenoxypyrazol-4-yl)methyleneaminooxymethyl]benzoate, N-4-tert-butylbenzyl-4-chloro-3-ethyl-1-methyl-5-pyrazolecarboxamide, tetranactin, dinactin, trinactin, 5-chloro-N-[2-[4-(2-ethoxyethyl)-2,3-dimethylphenoxy] ethyl]-6-ethylpyrimidin-4-amine], milbemectin, abamectin, ivermectin, azadirachtin [AZAD], 5-methyl[1,2,4]triazolo [3,4-b]benzothiazole, methyl 1-(butylcarbamoyl) benzimidazol-2-carbamate, 6-(3,5-dichloro-4-methylphenyl)-3(2H)-pyridazinone, 1-(4-chlorophenoxy)-3,3-dimethyl-1-(1H-1,2,4-triazol-1-yl)butanone, (E)-4-chloro-2-(trifluoromethyl)-N-[1-(imidazol-1-yl)-2-propoxyethylidene]aniline, 1-[N-propyl-N-[2-(2,4,6-trichlorophenoxy)ethyl]carbamoyl]imidazole, (E)-1-(4-chlorophenyl)-4,4-dimethyl-2-(1H-1,2,4-triazol-1-yl)-1-penten-3-ol, 1-(4-chlorophenyl)-4,4-dimethyl-2-(1H-1,2,4-triazol-1-yl)pentan-3-ol, (E)-1-(2,4-dichlorophenyl)-4,4-dimethyl-2-(1H-1,2,4-triazol-1-yl)-1-penten-3-ol, 1-(2,4-dichlorophenyl)-4,4-dimethyl-2-(1H-1,2,4-triazol-1-yl) pentan-3-ol, 4-[3-(4-tert-butylphenyl)-2-methylpropyl]-2,6-dimethylmorpholine, 2-(2,4-dichlorophenyl)-1-(1H-1,2,4-triazol-1-yl)hexan-2-ol, O,O-diethyl O-2-quinoxalinyl phosphorothioate, O-(6-ethoxy-2-ethyl-4-pyrimidinyl) O,O-dimethyl phosphorothioate, 2-diethylamino-5,6-dimethylpyrimidin-4-yl dimethylcarbamate, 4-(2,4-dichlorobenzoyl)-1,3-dimethyl-5-pyrazolyl p-toluenesulfonate, 4-amino-6-(1,1-dimethylethyl)-3-methylthio-1,2,4-triazin-5(4H)-one, 2-chloro-N-[(4-methoxy-6-methyl-1,3,5-triazin-2-yl)aminocarbonyl] benzenesulfonamide, 2-methoxycarbonyl-N-[(4,6-dimethoxypyrimidin-2-yl)aminocarbonyl] benzenesulfonamide, 2-methoxycarbonyl-N-[(4,6-dimethylpyrimidin-2-yl)aminocarbonyl] benzenesulfonamide, 2-methoxycarbonyl-N-[(4-methoxy-6-methyl-1,3,5-triazin-2-yl)aminocarbonyl] benzenesulfoneminde, 2-ethoxycarbonyl-N-[(4-chloro-6-methoxypyrimidin-2-yl)aminocarbonyl] benzenesulfonamide, 2-(2-chloroethoxy)-N-[(4-methoxy-6-methyl-1,3-5-triazin-2-yl)aminocarbonyl] benzenesulfonamide, 2-methoxycarbonyl-N-[(4,6-dimethoxypyrimidin-2-yl)aminocarbonyl] phenylmethanesulfonamide, 2-methoxycarbonyl-N-[(4-methoxy-6-methyl-1,3,5-triazin-2-yl)aminocarbonyl] thiophene-3-sulfonamide, 4-ethoxycarbonyl-N-[(4,6-dimethoxypyrimidin-2-yl)aminocarbonyl]-1-methylpyrazole-5-sulfonamide, 2-[4,5-dihydro-4-methyl-4-(1-methylethyl)-5-oxo-1H-imidazol-2-yl]-3-quinolinecarboxylic acid, 5-ethyl-5,8-dihydro-8-oxo[1,3] dioxolo[4,5-g]quinoline-7-carboxylic acid, 2-[4,5-dihydro-4-methyl-4-(1-methylethyl)-5-oxo-1H-imidazol-2-yl]-5-ethyl-3-pyridinecarboxylic acid, methyl 6-(4-isopropyl-4-methyl-5-oxoimidazolin-2-yl)-m-toluate, methyl 2-(4-isopropyl-4-methyl-5-oxoimidazolin-2-yl)-p-toluate, 2-(4-isopropyl-4-methyl-5-oxoimidazolin-2-yl)nicotinic acid, N-(4-chlorophenyl)methyl-N-cyclopentyl-N'-phenylurea, (RS)-2-cyano-N-[(R)-1-(2,4-dichlorophenyl)ethyl]-3,3-dimethylbutyramide, N-(1,3-dihydro-1,1,3-trimethylisobenzofuran-4-yl)-5-chloro-1,3-dimethylpyrazole-4-carboxamide, N-[2,6-dibromo-4-(trifluoromethoxy)phenyl]-2-methyl-4-(trifluoromethyl)-5-thiazolecarboxamide, 2,2-dichloro -N-[1-(4-chlorophenyl) ethyl]-3-methylcyclopropanecarboxamide, methyl (E)-2-[2-[6-(2-cyanophenoxy)pyrimidin-4-yloxy]phenyl]-3-methoxyacrylate, 5-methyl-1,2,4-triazolo[3,4-b] benzothiazole, 3-allyloxy-1,2-benzoisothiazol-1,1-dioxide, diisopropyl 1,3-dithiolan-2-ylidenemalonate, O,O-dipropyl O-4-methylthiophenylphosphate, and so on.

The content of the pesticidal active ingredient is 0.1 to 75% by weight, usually 3 to 60% by weight, preferably 5 to 40% by weight in the present composition.

Examples of the dispersant in the present composition include lignosulfonate; naphthalenesulfonic acid-formalin condensate; copolymers of i) maleic acid or maleic anhydride and ii) isobutylene or diisobutylene; polycarboxylic acid; and copolymers of iii) styrene, styrenesulfonic acid or vinyl acetate and iv) acrylic acid, metacrylic acid or maleic anhydride. Further, the alkali metal salts (e.g. sodium salt, potassium salt), alkaline earth metal salts (e.g. calcium salt, magnesium salt), ammonium salts and organic ammonium salts (e.g. triethanolamine salt) of the above-mentioned compounds are also exemplified. The dispersant is contained in the present composition solely or combined two or more.

The content of the dispersant is 0.3 to 40% by weight, usually 3 to 30% by weight, preferably 5 to 20% by weight in the present composition.

Example of the wetting agent in the present composition include dialkyl sulfocarboxylic acid esters; alkyl or dialkylnaphthalenesulfonic acids; alkyl sulfates; alkyl phosphates; sulfoalkylamides; carboxylates; α-olefinesulfonates; dialkyl sulfosuccinates; alkyl ether sulfuric acid esters; alkyl phenyl ether sulfuric acid esters; aryl phenyl ether sulfuric acid esters such as styryl phenyl ether sulfates, distyryl phenyl ether sulfates, tristyryl phenyl ether sulfates, etc.; alkyl ether phosphoric acid esters; alkyl phenyl ether phosphoric acid esters; aryl phenyl ether phosphoric acid esters such as styryl phenyl ether phosphates, distyryl phenyl ether phosphates, tristyryl phenyl ether phosphates, etc.; polyoxyalkylene alkyl ether sulfuric acid esters such as polyoxyethylene alkyl ether sulfates, etc,; polyoxyalkylene alkyl phenyl ether sulfuric acid esters such as polyoxyethylene nonyl phenyl ether sulfates, etc.; polyoxyalkylene aryl phenyl ether sulfuric acid esters such as polyoxyethylene styryl phenyl ether sulfates, polyoxyethylene distyryl phenyl ether sulfates, polyoxyethylene tristyryl phenyl ether sulfates, etc.; polyoxyalkylene alkyl ether phosphoric acid esters such as polyoxyethylene nonyl ether phosphates, etc.); polyoxyalkylene alkyl phenyl ether phosphoric acid esters such as polyoxyethylene nonyl phenyl ether phosphates, etc.; polyoxyalkylene aryl phenyl ether phosphoric acid esters such as polyoxyethylene styryl phenyl ether phosphates, polyoxyethylene distyryl phenyl ether phosphates, polyoxyethylene tristyryl phenyl ether phosphates, etc.; and alkali metal salts (e.g. sodium salt, potassium salt), alkaline earth metal salts (e.g. calcium salt, magnesium salt), ammonium salts and organic ammonium salts (e.g. triethanolamine salt) thereof.

Further, exemplified are ethoxylated acetylenediols, polyethylene oxides, polypropylene oxides, polyoxyalkylene alkyl ethers, polyoxyalkylene alkyl phenyl ethers, polyoxyalkylene alkyl aryl ethers, polyoxyethylenepolyoxypropylene alkyl aryl ethers, polyoxyethylenefatty acid esters, polyvalent alcohol fatty acid esters, polyoxyethylene polyvalent alcohol fatty acid esters, sorbitanfatty acid ester alkoxylates, castor oil alkoxylates, polyoxyethylene carboxylic acid esters, polyoxyethylene polyoxypropylene block copolymers and polyoxyethylene alkylamines.

The wetting agent is contained in the present composition solely or combined two or more. The content of the wetting agent is 0.3 to 20% by weight, preferably 1 to 20% by weight in the present composition.

Among these wetting agents, preferable are alkyl or dialkylnaphthalenesulfonic acids, alkyl sulfates, alkyl phosphates, carboxylates, α-olefinesulfonates, dialkyl sulfosuccinates, alkyl ether sulfuric acid esters, alkyl phenyl ether sulfuric acid esters, alkyl ether phosphoric acid esters, alkyl phenyl ether phosphoric acid esters, polyoxyalkylene alkyl ether sulfuric acid esters, polyoxyalkylene alkyl phenyl ether sulfuric acid esters, polyoxyalkylene aryl phenyl ether sulfuric acid esters, polyoxyalkylene alkyl ether phosphoric acid esters, polyoxyalkylene alkyl phenyl ether phosphoric acid esters, polyoxyalkylene aryl phenyl ether phosphoric acid esters, and alkali metal salts, alkaline earth metal salts, ammonium salts and organic ammonium salts (e.g. triethanolamine salt) thereof. Further, acetylenediols, polyoxyalkylene alkyl phenyl ethers, fatty acid alkoxylates, polyoxyalkylene alkyl ethers, sorbitanfatty acid ester alkoxylates, castor oil alkoxylates and so on are also preferable.

When the present composition is water dispersible granule or water dispersible tablet, the combination of the following component (1) and (2) among the above-mentioned preferable wetting agents is very effective because of good productivity and rapid disintegrability in water.

Component (1)

alkyl and dialkylnaphthalenesulfonic acids, polyoxyalkylene alkyl ether sulfuric acid esters, polyoxyalkylene alkyl phenyl ether sulfuric acid esters, polyoxyalkylene aryl phenyl ether sulfuric acid esters, polyoxyalkylene alkyl ether phosphoric acid esters, polyoxyalkylene alkyl phenyl ether phosphoric acid esters, polyoxyalkylene aryl phenyl ether phosphoric acid esters, and their alkali metal salts, alkaline earth metal salts, ammonium salts and organic ammonium salts (e.g. triethanolamine salt)

Component (2)

alkyl sulfates, alkyl phosphates, carboxylates, α-olefinesulfonates, dialkyl sulfosuccinates, alkyl ether sulfuric acid esters, alkyl phenyl ether sulfuric acid esters, alkyl ether phosphoric acid esters, alkyl phenyl ether phosphoric acid esters, their alkali metal salts, alkaline earth metal salts, ammonium salts and amine salts, acetylenediols, polyoxyalkylene alkyl phenyl ethers, fatty acid alkoxylates, polyoxyalkylene alkyl ethers, sorbitanfatty acid ester alkoxylates and castor oil alkoxylates The weight ratio of the dispersant and the wetting agent in the present composition is preferably 1:9 to 9:1, and the total amount of the dispersant and the wetting agent in the present composition is usually 0.6 to 50% by weight, preferably 1 to 30% by weight, more preferably 3 to 20% by weight.

The boron compound which can be used in the present invention is boron oxide, boric acid, borate or mixture thereof.

Typical example of the boron oxide is diboron trioxide ($B_2O_3$). Examples of the boric acid include orthoboric acid ($H_3BO_3$), tetraboric acid ($H_2B_4O_7$), metaboric acid ($HBO_2$) and condensed acids such as pyroboric acid and examples of the borate include alkali orthoborates such as sodium orthoborate and borax, alkaline earth orthoborates, and ammonium borates such as ammonium orthoborate. Anhydrous boron compounds are preferably used.

The particle diameter and shape of the boron compound are designed or selected suitably for the type of the present formulation. A lump of the boron compound is pulverized to a suitable size, usually powders. When the present formulation is used for diluting with water and spraying, the boron compound should be finely pulverized for preventing clogging of spray nozzle, and its particle size is usually 300 µm or less, preferably 100 µm or less, more preferably 40 µm or less.

Further, the boron compound is preferably non-deliquescent in view of hygroscopicity in production and stability of the formulation after opening a sealed package.

Examples of the water-soluble carrier include water-soluble polymers such as polyvinyl alcohol, polyvinylpyrrolidone, polyethylene glycol, polypropylene glycol, copolymer of polyethylene glycol and polypropylene glycol; saccharides such as lactose, sucrose and modified starch; salts, namely alkali metal salts, alkaline earth metal salts, ammonium salts, organic ammonium salts of inorganic acids and organic acids such as sulfuric acid, hydrochloric acid, nitric acid, carbonic acid, phosphoric acid, pyrophosphoric acid, lactic acid, tartaric acid, succinic acid, butyric acid and malic acid; and urea.

These water-soluble carriers can be used solely or combined two or more. The content of the water-soluble carrier in the present formulation is 0.1 to 95% by weight, preferably 1 to 75% by weight, more preferably 1 to 55% by weight.

Smectite is a clay mineral and generally has dioctahedral and trioctahedral structure. Examples of the smectite include montmorillonite, saponite, beidellite, hectorite, sauconite, nontronite. Bentonite, which is a clay mineral containing montmorillonite as a main component, is preferably used. The content of the smectite in the present formulation is 0.1 to 30% by weight, preferably 0.1 to 20% by weight.

The present formulation may contain a solvent, if necessary.

The solvents are exemplified by paraffin, aromatic hydrocarbon, polar solvents, animal oils and vegetable oils. Examples of the paraffin include normalparaffins, isoparaffins, cycloparaffins, liquid paraffin and naphthanes. Examples of the aromatic hydrocarbon include xylene, alkylbenzenes, alkylnaphthalenes, phenylxylylethane and diphenylxylylethane. Examples of the polar solvent include ketones such as cyclohexanone, heptanone, octanone, nonanone and acetophenone; N-methyl-2-pyrrolidone; esters such as hexyl acetate, benzyl acetate, phenylethyl acetate, benzyl benzoate, methyl benzoate, isobutyl oleate, benzyl salycilate, butylcyclohexyl acetate, methybenzyl acetate, methyl oleate, methyl laurate, mono- or diesters of dicarboxylic acid including diisodecyl phthalate, dioctyl phthalate, diisodecyl adipate, diisobutyl adipate and isobutyl adipate; alcohols such as ethylene glycol, propylene glycol, benzyl alcohol, phenylethyl alcohol, butylcyclohexanol, phenyloxyethanol and higher alcohols including oleyl alcohol and stearyl alcohol; fatty acids, usually having carbon number of 6 to 9, such as caproic acid, caprylic acid and pelargonic acid; and silicone oil and derivatives thereof. Examples of the animal oil and vegetable oil include rapeseed oil, soybean oil and linseed oil.

The solvent can be used solely or combined two or more.

Especially, the solvent having 100° C. or more of flash point is preferable, and more preferable is the solvent having 150° C. or more.

The content of the solvent is suitably designed for the objects such as improving of handling in preparation of the formulation, preventing precipitation of crystals in preservation at low temperature, and increasing efficacy.

When the pesticidal active ingredient is solid at room temperature, the content of the solvent in the present formulation is usually 50% by weight or less, preferably 30% by weight or less, more preferably 20% by weight or less.

When the pesticidal active ingredient is liquid or semi-solid at room temperature, the content of the solvent in the present formulation is suitably designed depending on the objects such as handling in preparation, adjusting viscosity of the pesticidal active ingredient, preventing precipitation of crystals in preservation at low temperature, and adjusting efficacy, and is usually 40% by weight or less, preferably 30% by weight or less, more preferably 20% by weight or less in the present formulation.

When the present formulation contains the solvent or the pesticidal active ingredient utilized in the present formulation is liquid at ordinary temperature, a water-insoluble carrier such as precipitated silica, pyrogenic silica and attapulgite may be used because the water-insoluble carrier acts as a support of the liquid part in the present formulation. Among them, water-insoluble carriers having high absorptive power of oil such as silica are convenient. The content of the water-insoluble carrier is usually 10 to 300 parts by weight, preferably 20 to 170 parts by weight based on 100 parts by weight of the total liquid part, for example, sum of solvent and components dissolved in the solvent.

When the present formulation is granule, a hydrophobic substance or water repellent can be contained in the present formulation for the purpose of preventing precipitation in water and accelerating dispersion when diluting the present formulation with water.

Typical examples of the hydrophobic substance or water repellent include fatty acids having 10 or more carbon number such as capric acid, lauric acid, stearic acid and oleic acid; metal salts of fatty acid such as calcium stearate, magnesium stearate, sodium stearate, zinc stearate, aluminum stearate and barium stearate; solid substances such as paraffin powder, various waxes, and hydrophobic silica exemplified by Aerosil R972, Aerosil R974 and Aerosil R976 produced by Nippon Aerosil Corp.

The content of the hydrophobic substance or water repellent is usually 10% by weight or less. An addition of the hydrophobic substance or water repellent to the present formulation is usually performed by mixing with the other components. When the hydrophobic substance or water repellent is liquid, it is practically beneficial that powders are mixed with the other components after the hydrophobic substance or water repellent is absorbed to the powders.

The solid present formulation may contain optionally additives such as preservative, binder, stabilizer, agent increasing efficacy such as quarternary ammonium ions, coloring agent such as Rhodamine and Acid Blue, perfume and lubricant.

The present formulation is a solid formulation, namely, powdery formulations such as dust and wettable powder; granulated formulations such as granule, water dispersible granule, tablet and capsule: and so on. It is preferably, a formulation for diluting with water before application such as wettable powder, water dispersible granule and tablet in view of the components. Further, granulated formulation and tablet are preferable to powdery formulation in view of handling, safety and environment sanitation.

Granulated formulations can be obtained by granulating the present powdery formulations. Their shape depends on the granulating method and is cylindrical, sphere, and so on, and may be indeterminate form. Tablets are prepared by pressing the present powdery or granulated formulation to form a designated shape, and the shape is various and may be simple, angular or round-rim disk, thin or thick lens, pillow-, almond- or finger-shape, triangle, square, pentagon or corn-shape.

The preparation methods of the present powdery formulation are given below.

When the pesticidal active ingredient is solid, the present formulation can be prepared by pulverizing the pesticidal active ingredient by dry pulverizer such as pin mill, hammer mill, impact grinder, ball mill and jet-o-miser; adding dispersant, wetting agent, water-soluble carrier, smectite, the boron compound, optionally solvent, water-insoluble carrier and the other additive to the pulverized product; and mixing them by a mixer such as ribbon mixer and Nauta mixer. A part or all of the components except the pesticidal active ingredient may be mixed with the pesticidal active ingredient before pulverizing.

When the pesticidal active ingredient is liquid, the pesticidal active ingredient, as it is or after preparing a solution by dissolving it with a solvent, is mixed with a carrier by a mixer such as ribbon mixer and Nauta mixer and pulverized by a dry pulverizer such as pin mill and hammer mill. The amount of the carrier is usually 10 to 500 parts by weight, preferably 20 to 300 parts by weight based on 100 parts by weight of the pesticidal active ingredient or its solution. To the pulverized product obtained above, dispersant, wetting agent, water-soluble carrier, smectite, the boron compound, optionally solvent, water-insoluble carrier and the other additive are added and mixed by the above-mentioned mixer to give the present formulation. A part or all of the components except the components mixed before pulverizing may be mixed in advance.

When the pesticidal active ingredient is semi-solid, the pesticidal active ingredient can be liquid by addition of a solvent or heat and dealt according to the case that the pesticidal active ingredient is liquid to give the present formulation.

The granulating methods for preparing the present granular formulation are explained below.

The granulating method is not specific and exemplified by dry granulation method, wet extrusion granulation method, spray-dry method and fluidized bed granulation method.

In dry granulation method, the present powdery formulation obtained above is made to sheet, pillow granule or slug by dry granulator such as roller compacter and bricketting machine or slug machine, and pulverized or broken by spherizer or the like. The present granular formulation can be used as it is, but may be subjected to spherical procedure by Marumelizer (produced by Fuji paudal Co., Ltd.) or the like for preventing powdering at transportation and application. When dry granulator is used, the powdery formulation is set between the rollers and pressed at 30 kg/cm$^2$ or more, preferably 50 kg/cm$^2$ or more. The diameter of the granular formulation is usually in the range of about 10000 to 100 μm, preferably about 4000 to 297 μm.

Typical wet piston granulation method is explained below.

To the present powdery formulation obtained above, 5 to 50% by weight of water based on the present powdery formulation is added and kneaded by mortar, Nauta mixer, kneader or the like. The kneaded product is granulated by extrusion granulator such as basket type extruder, horizontal type extruder and Twin-dome gran (produced by Fuji paudal Co., Ltd.) to give granules. The diameter of the throat area of the screen is usually about 0.3 to 2 mm, preferably 0.5 to 1.5 mm in view of industrial production. In this case, the obtained granules are cylindrical shape of about 0.01 to 3 mm in diameter and 0.3 to 10 mm in length. The obtained granules are dried at room temperature to 150° C. by a drier such as fluidized bed drier to give the present formulation. If the present formulation comprises liquid or volatile substance, the drying condition such as drying temperature and wind speed is adjusted depending on the property thereof.

In this case, it is better to contact the boron compound with water in short time, especially it is desired to complete granulating and drying within 3 hours after the addition of water. It is preferably within 2 hours, more preferably within 1 hour.

Further, water may be added to the components without the boron compound and then the boron compound may be mixed with them before granulation. Even in this case, the time from mixing the boron compound to granulation and drying is desired to be within 3 hours, preferably within 2 hours, more preferably within 1 hour.

Tablet is obtained by pressing each of a designated amount of powdery present formulation in mortar, industrially by pressing the above powdery or granular present formulation by tablet machine or bricketting machine to give a designated weight of the tablet continuously. A size of the tablet can be adjusted depending on the applied method and is usually about 7 to 60 mm in diameter and about 1 to 40 mm in thickness, and about 0.1 to 100 g, preferably about 1 to 50 g in weight per one tablet.

When these formulations are powdery formulations or formulations obtainable by dry granulation method, it is preferable to set a content of the present compound much larger than the formulations obtainable by wet granulation method including drying step, because water is carried over from dispersant, wetting agent, carrier and so on.

Among wet granulation methods, tumbling granulation method and extrusion granulation method are preferable.

In fluidized bed granulation method, it is preferable that the powdery present formulation is put in a granulator and a binder solution or water is sprayed. In view of practical production, though the formulation contacts with more water than dry granulation method on account of water carried over from dispersant, wetting agent, carrier and so on, wet granulation method including drying step in the process is preferable as the contact time with water is relatively short.

The present formulation is used for controlling pests, regulating plant growth and so on. The application method is exemplified by methods for applying it to paddy field in flooding condition, river, pond, farm, lawn, orchard, non-cultivated field and so on as it is, or applying it to crops or soil with a sprayer after diluting with water to a suitable concentration.

When the present formulation is applied to paddy field in flooding condition, the dosage is varied depending on a kind and amount of the active ingredient, and is usually about 0.1 to 200 g, preferably about 1 to 100 g per 1 hectare. When the present formulation is applied to paddy field in flooding condition as it is, any special devices are usually not needed. For example, a person in the paddy field may apply the formulation uniformly or at one or more points. Further, it may be applied from the outside of the paddy field such as applications in the neighborhood of a ridge between paddy fields, at paddy water inlet and from a ridge between paddy fields. Furthermore, it can be applied with a power applicator (power granule applicator) from a ridge between paddy fields and in aerial application by helicopter, plane or radio-controlled plane.

The application time is varied depending on a kind of active ingredient, but is usually between a time immediately after plow a paddy field in preparation for transplanting young rice plant and about two weeks after earing. The application time of the present formulation containing a herbicidal active ingredient is generally between a time immediately after plow a paddy field in preparation for transplanting young rice plant and about 15 days after rice-planting.

On the other hand, when the present formulation is applied to river, pond, farm, lawn, orchard and non-cultivated field, any special devices are usually not needed like an application to paddy field in flooding condition. For example, a person in the river, pond, farm, lawn, orchard and non-cultivated field may apply the formulation uniformly or from riverside or edge of pond. Further, it can be applied with a power applicator (power granule applicator) from a ridge between paddy fields and in aerial application by helicopter, plane or radio-controlled plane.

When it is used after diluting with water, the dilution ratio depends on a kind of the pesticidal active ingredient in the present formulation, content, kind of the objective pest and application condition, and is usually about 2 to 10000 times, preferably 50 to 8000 times, more preferably 500 to 4000 times. The application can be performed with an applicator such as knapsack type power applicator, boom sprayer and speed sprayer, or in aerial application by helicopter, plane, radio-controlled plane or the like.

The package of the present formulation may be available package for usual granules or wettable powders such as aluminum bag, paper bag, paper container and so on. Preventing from moisture absorption while preserving, aluminum bag, paper bag coated with aluminum insides, resin bag and so on are preferably used. Further, packing water-soluble envelope with these bags is expected preventing moisture while preserving, increasing safety, increasing convenience while diluting, and so on.

EXAMPLES

Hereinafter, the present invention is explained in more detail referring to examples but the present invention should not be limited in the following examples.

Example 1

9.2 parts by weight of (RS)-α-cyano-3-phenoxybenzyl (1RS)-cis, trans-3-(2,2-dichlorovinyl)-2,2-dimethylcyclopropanecarboxylate and 10 parts by weight of Hisol SAS-296 (phenylxylylethane, organic solvent produced by Nippon Petrochemicals Company) were heated to about 50° C. to afford a mixed solution. The mixed solution was added to 10 parts by weight of SIPERNAT 50S (white carbon produced by Degussa Corp.), and mixed homogeneously and pulverized by juice mixer to afford fine powders. To the fine powders, 12 parts by weight of copolymer of diisobutylene with maleic anhydride and potassium polyoxyethylenearyl phenyl ether sulfate (Geropon SC-213, surfactant produced by Rodia Nikka Company), 2 parts by weight of sodium dodecylbenzenesulfonate, 10 parts by weight of bentonite, 5 parts by weight of metaboric acid (produced by Kanto Chemical Company) and sucrose to make the total 100 parts by weight, and mixed and pulverized by juice mixer to afford 200 g of mixed powders. The mixed powders were put in a mortar, and 10 parts by weight of ion-exchanged water were mixed with 100 parts by weight of the mixed powders and kneaded. The kneaded product is granulated with a single dome gran with screen having 0.5 mm in diameter (extrusion granulator produced by Fuji-Powdal), dried at 60° C. for 20 minutes and sieved to afford a water dispersible granule having 300 to 710 mm in diameter.

Example 2

The same procedure was performed as Example 1, except that 14 parts by weight of Carplex 80D (white carbon produced by Shionogi & Co.) was used in place of 10 parts by weight of SIPERNAT 50S and 2.5 parts by weight of metaboric acid (produced by Kanto Chemical Company) was used in place of 5 parts by weight, to afford a water dispersible granule having 300 to 710 mm in diameter.

Example 3

The same procedure was performed as Example 2, except that boron oxide (first grade agent produced by Wako Chemical Company) was used in place of metaboric acid (produced by Kanto Chemical Company), to afford a water dispersible granule having 300 to 710 mm in diameter.

Example 4

The same procedure was performed as Example 3, except that the content of boron oxide was changed from 2.5 parts by weight to 5 parts by weight, to afford a water dispersible granule having 300 to 710 mm in diameter.

Example 5

The same procedure was performed as Example 3, except that the screen of single dome gran (extrusion granulator produced by Fuji-Powdal) was changed from 0.5 mm in diameter to 0.6 mm in diameter, to afford a water dispersible granule having 300 to 850 mm in diameter.

Example 6

The same procedure was performed as Example 5, except that the content of boron oxide was changed from 2.5 parts by weight to 5 parts by weight, to afford a water dispersible granule having 300 to 850 mm in diameter.

Reference Example 1

9.3 parts by weight of (RS)-α-cyano-3-phenoxybenzyl (1RS)-cis, trans-3-(2,2-dichlorovinyl)-2,2-dimethylcyclopropanecarboxylate and 10 parts by weight of Hisol SAS-296 (phenylxylylethane, organic solvent produced by Nippon Petrochemicals Company) were heated to about 50° C. to afford a mixed solution. The mixed solution was added to 10 parts by weight of SIPERNAT 50S (white carbon produced by Degussa Corp.), and mixed homogeneously and pulverized by juice mixer to afford fine powders. To the fine powders, 12 parts by weight of copolymer of diisobutylene with maleic anhydride and potassium polyoxyethylenearyl phenyl ether sulfate (Geropon SC-213, surfactant produced by Rodia Nikka Company), 2 parts by weight of sodium dodecylbenzenesulfonate, 10 parts by weight of bentonite, 2 parts by weight of calcium stearate and sucrose to make the total 100 parts by weight, and mixed and pulverized by juice mixer to afford 200 g of mixed powders. The mixed powders were put in a mortar, and 12 parts by weight of ion-exchanged water were mixed with 100 parts by weight of the mixed powders and kneaded. The kneaded product is granulated with Single-dome gran with screen having 0.5 mm in diameter (extrusion granulator produced by Fuji paudal Co., Ltd.), dried at 50° C. for 20 minutes and sieved to afford a water dispersible granule having 300 to 710 mm in diameter.

Test Example

About two grams (2 g) of the water dispersible granule sample obtained by Example 3 were spread on a glass petri-dish and left at room temperature (25° C., relative humidity: about 50%) for one hour.

Each of the sample left at room temperature (Sample 1) and the sample closed immediately after production (Sample 2) was sealed in aluminum bag and preserved in the thermostat of 54° C. for 2 weeks. Disintegration in water of the sample obtained by preserving Sample 1 at 54° C. (Sample 11) and the sample obtained by preserving Sample 2 at 54° C. (Sample 21) was evaluated.

The disintegration in water of the water dispersible granules obtained by Example 4 and Reference Example 1 was also evaluated.

Disintegration Test in Water

In 250-ml cylinder with a stopper, 250 ml of 342 ppm hard water were charged and kept at 20° C. in a constant-temperature water. Thereafter, 500 mg of water dispersible granule was put in the cylinder, which was then turned upside down. This upside-down turning was repeated at a rate of once per one second. The evaluation was performed by counting the number of repetition of upside-down turning of the cylinder required to complete disintegration and dispersion of the water dispersible granule.

Indication Method (Actual Turning Number is Indicated in the Parenthesis.)

TABLE 1

| Number of overturn | Indication |
|---|---|
| 10–17 | ◎ |
| 18–25 | ○ |
| 26–33 | Δ |
| 34–41 | x |
| 42- | xx |

| Examples | Sample 2 | Sample 21 | Sample 11 |
|---|---|---|---|
| Example 3 | ◎ (14) | ◎ (15) | ○(18) |
| Example 4 | ◎ (13) | ◎ (15) | ○(20) |
| Reference Example 13 | ◎ (15) | ◎ (14) | XX (50 or more) |

The present invention provides a solid formulation that is excellent in preservation stability and can prevent aggregation of formulation, reducing of fluidity, and reducing dispersibility when water dispersible granule is diluted with water.

I claim:

1. A solid pesticidal formulation which comprises
   (a) 0.1 to 75% by weight of a pesticidal active ingredient,
   (b) 0.3 to 40% by weight of a dispersant,
   (c) 0.3 to 20% by weight of a wetting agent,
   (d) 0.1 to 30% by weight of a boron compound selected from the group of boron oxide, boric acid and borate,
   (e) 0.1 to 95% by weight of a water-soluble carrier and
   (f) 0.1 to 30% by weight of smectite.

2. The solid pesticidal formulation according to claim 1, wherein the content ratio of the dispersant and the wetting agent is 1:9 to 9:1 and the total content of the dispersant and the wetting agent is 0.6 to 50% by weight.

3. The solid pesticidal formulation according to claim 1, wherein the dispersant is at least one selected from the following group (b1) and (b2):
   (b1) lignosulfate; naphthalenesulfonic acid-formalin condensate; copolymers of i) maleic acid or maleic anhydride and ii) isobutylene or diisobutylene; polycarboxylic acid; and copolymers of iii) styrene, styrenesulfonic acid or vinyl acetate and iv) acrylic acid, metacrylic acid or maleic anhydride
   (b2) alkali metal salts, alkaline earth metal salts, ammonium salts and organic ammonium salts of the compounds given in (b1).

4. The solid pesticidal formulation according to claim 1, wherein the solid formulation is water dispersible granule.

5. The solid pesticidal formulation according to claim 1, wherein the boron compound is boron oxide.

6. The solid pesticidal formulation according to claim 1, wherein the boron compound is diboron trioxide.

7. The solid pesticidal formulation according to claim 1, wherein the boron compound is boric acid.

8. The solid pesticidal formulation according to claim 1, wherein the boron compound is orthoboric acid.

9. The solid pesticidal formulation according to claim 1, wherein the boron compound is metaboric acid.

10. The solid pesticidal formulation according to claim 1, wherein the boron compound is borate.

11. The solid pesticidal formulation according to claim 1, wherein the boron compound is alkali orthoborate.

12. The solid pesticidal formulation according to claim 1, wherein the boron compound is alkaline earth orthoborate.

13. The solid pesticidal formulation according to claim 1, wherein the boron compound is ammonium orthoborate.

14. The solid pesticidal formulation according to claim 1, wherein the water-soluble carrier is a saccharide.

15. The solid pesticidal formulation according to claim 1, wherein the smectite is bentonite.

* * * * *

UNITED STATES PATENT AND TRADEMARK OFFICE
CERTIFICATE OF CORRECTION

PATENT NO. : 6,596,292 B2
DATED : July 22, 2003
INVENTOR(S) : Shugo Nishi

It is certified that error appears in the above-identified patent and that said Letters Patent is hereby corrected as shown below:

<u>Column 13, lines 39-44 and Column 14, lines 1-2,</u>
Amend Claim 1 as follows:

1. (Amended) A solid pesticidal formulation which comprises:

(a) 0.1 to 75% by weight of a pesticidal active ingredient, (b) 0.3 to 40% by weight of a dispersant, (c) 0.3 to 20% by weight of a wetting agent, (d) 0.1 to 30% by weight of a boron compound selected from the group consisting of boron oxide, boric acid, and borate, (e) 0.1 to 95% by weight of a water-soluble carrier and (f) 0.1 to 30% by weight of smectite.

<u>Column 14,</u>
Lines 20-21, amend claim 4 as follows:

4. (Amended) The solid pesticidal formulation according to claim 1, wherein the solid formulation is a water dispersible granule.

Signed and Sealed this

Twenty-eighth Day of September, 2004

JON W. DUDAS
*Director of the United States Patent and Trademark Office*